United States Patent [19]

Pucci et al.

[11] Patent Number: 5,348,624
[45] Date of Patent: Sep. 20, 1994

[54] PROCESS FOR SEPARATING ETHYL TERT-BUTYL ETHER AND ETHANOL

[75] Inventors: Annick Pucci, Croissy sur Seine; Paul Mikitenko, Noisy le Roi; Massimo Zuliani, Rueil Malmaison, all of France

[73] Assignee: Institut Francais du Petrole, Rueil Malmaison, France

[21] Appl. No.: 974,763

[22] Filed: Nov. 12, 1992

[30] Foreign Application Priority Data

Nov. 12, 1991 [FR] France ................... 91 14062

[51] Int. Cl.$^5$ ........................... B01D 3/34
[52] U.S. Cl. ..................... 203/14; 203/19; 203/46; 203/63; 203/75; 203/76; 203/77; 203/78; 203/79; 203/80; 203/99; 203/DIG. 9; 203/DIG. 13; 203/DIG. 19; 568/913; 568/916; 568/918
[58] Field of Search ............... 203/19, 14, 46, 63, 203/75, 77, 76, 79, 78, 80, 99, DIG. 9, DIG. 13, DIG. 19; 202/204; 568/697, 918, 913, 916, 917

[56] References Cited

U.S. PATENT DOCUMENTS

| | | | |
|---|---|---|---|
| 2,354,897 | 8/1944 | Wentworth | 202/161 |
| 2,489,619 | 11/1949 | Carlson et al. | 202/42 |
| 4,014,667 | 3/1977 | Barber | 203/18 |
| 4,336,407 | 6/1982 | Smith, Jr. | 203/DIG. 6 |
| 4,349,415 | 9/1982 | De Filippi et al. | 203/19 |
| 4,349,416 | 9/1982 | Brandt et al. | 203/19 |
| 4,428,798 | 1/1984 | Zudkevitch et al. | 203/19 |
| 4,440,601 | 4/1984 | Katz et al. | 203/19 |
| 4,440,963 | 4/1984 | Childs | 203/67 |
| 4,482,768 | 11/1984 | Somekh | 568/918 |
| 4,770,780 | 9/1988 | Moses | 203/16 |
| 5,015,783 | 5/1991 | Vora et al. | 568/697 |
| 5,059,288 | 10/1991 | Curry | 203/43 |

FOREIGN PATENT DOCUMENTS

| | | |
|---|---|---|
| 0071032 | 2/1983 | European Pat. Off. . |
| 3142518 | 5/1983 | Fed. Rep. of Germany ........ 203/19 |
| 3447615 | 7/1985 | Fed. Rep. of Germany ........ 203/19 |

OTHER PUBLICATIONS

Kirk–Othmer Encyclopedia of Chemical Technology, Third Edition, Supplement Volume, Alcohol Fuels to Toxicology, John Wiley & Sons, New York, pp. 150–153.

*Primary Examiner*—Virginia Manoharan
*Attorney, Agent, or Firm*—Millen, White, Zelano, & Branigan

[57] ABSTRACT

For separating ETBE and ethanol the following principal stages are employed:

(1) Extraction of ethanol by water, the raffinate being ETBE saturated in water and the extract an ethanol/water mixture containing a small proportion of ETBE;

(2) Concentration of the above mixture, the distillate being a mixture close to the ethanol/water azeotrope in composition and containing a very small proportion of ETBE;

(3) Heteroazeotropic distillation of this distillate in two coupled columns with an overhead decanter, this distillation using ETBE as azeotroping agent; the residue of the first column being ethanol which is ca. 99% by mole and the residue of the second column being practically pure water, this water and the water recovered during the concentration stage being used as extraction solvent in stage (1).

Stage (3) may be an ethanol dehydration unit using ETBE as dehydrating agent.

21 Claims, 1 Drawing Sheet

PROCESS FOR SEPARATING ETHYL TERT-BUTYL ETHER AND ETHANOL

BACKGROUND OF THE INVENTION

The invention relates to the production of ethyl tert-butyl ether (abbreviated to ETBE) and more particularly its separation from mixtures with ethanol.

It is known that ethyl tert-butyl ether, like methyl tert-butyl ether (abbreviated to MTBE), can be used as a high-octane additive for lead-free or reduced-lead gasolines. Provision can be made to add ETBE to gasolines in concentrations ranging for example up to ca. 15% by volume.

A process for producing MTBE involves performing a reaction adding methanol to isobutene, contained for example in a steam-cracking, catalytic cracking or isobutane dehydrogenation $C_4$ cut. After reaction, the residual methanol is generally separated by azeotropic distillation with $C_4$ hydrocarbons, which allows the MTBE to be obtained fairly easily with a degree of purity which is suitable for its addition to gasolines.

ETBE can be produced by a similar process, with ethanol replacing methanol. Such a process is described e.g. in "ETBE, a future for ethanol" by A. Forestiere, B. Torck and G. Pluche, a paper at the Biomass for Energy and Industry Conference, Lisbon, 9–13 Oct. 1989, and in "MTBE/ETBE, an Incentive Flexibility for Refiners", by A. Forestiere and coll., a paper at the "Conference on Oxygenated Fuels in Europe", London, 22–23 May 1990.

However, with such a process, contrary to the case of MTBE, after elimination of the $C_4$ hydrocarbons, almost all the residual ethanol is mixed with the ETBE produced. The existence of an ethanol/ETBE azeotrope containing 21% by weight ethanol at atmospheric pressure, boiling at 66.6 degrees C, makes it difficult to separate the ETBE with a degree of purity sufficient to meet the specifications relating to the ethanol content of gasolines. Thus, the ethanol content of the ETBE must generally be between 0.5 and 10% by weight. Advantageously, the ETBE will have to be purified to 2% by weight of ethanol for dispatch to the refinery.

Thus, for ETBE to compete with MTBE as an additive improving the octane rating of lead-free gasolines, it was particularly desirable to find an economically attractive separation process. This is what the invention proposes.

SUMMARY OF THE INVENTION

The subject of the invention is thus a process for separating ETBE from mixtures which it forms with ethanol, and more particularly from the ETBE/ethanol mixtures resulting from the reaction of ethanol on a catalytic steam-cracking or isobutane dehydrogenation $C_4$ cut.

The subject of the invention is also a process for producing ETBE including such a separation operation and in which the ethanol is recycled to the etherification reactor.

The process of the invention for separating ETBE and ethanol applies in general to mixtures comprising essentially ethanol and ETBE in various proportions, and more particularly to mixtures resulting from the reaction adding ethanol to the isobutane contained in a steam-cracking, catalytic cracking or isobutane dehydrogenation $C_4$ cut, which generally contain ca. 5 to 50%, most often 10 to 30% by weight of ethanol.

The process of the invention for separating ethyl tert-butyl ether, based overall on the implementation of an extraction with water, a concentration and a heteroazeotropic distillation in two coupled columns with an overhead decanter, can be defined generally by the fact that it comprises:

(1) an extraction stage in which a charge, essentially comprising a mixture of ethyl tert-butyl ether and ethanol, is introduced into an extraction zone into which water is introduced as extraction solvent and from which there is collected a raffinate, essentially comprising ethyl tert-butyl ether saturated in water, and an extract comprising an ethanol/water mixture containing a small proportion of ethyl tert-butyl ether;

(2) a concentration stage in which the extract from stage (1) is sent into a concentration zone From which a distillate close to the azeotropic ethanol/water composition is collected at the head, and a residue comprising essentially water at the base, and a phase is drawn off, comprising essentially ethyl tert-butyl ether, which is combined with the raffinate of extraction stage (1); and (3) a heteroazeotropic distillation stage using ethyl tert-butyl ether as azeotroping agent, in which the distillate from the said concentration stage is sent into a first distillation zone from which a residue essentially comprising ethanol is collected, the vapor emerging overhead being combined with the head vapor from a second distillation zone, the resultant vapor being condensed and sent into a decanter where separation takes place into an upper phase, rich in ethyl tert-butyl ether, which is sent in reflux to the head of the said first distillation zone, and a lower phase, rich in water, which is returned in reflux to the head of the said second distillation zone, and whose residue essentially comprises water, which is sent, after combining with the residue of the said concentration zone and possible supplement, to feed the head of the said extraction zone, ethyl tert-butyl ether being introduced into the decanter during the start-up of the process.

BRIEF DESCRIPTION OF THE DRAWINGS

The conditions of realization of the process of the invention are described in more detail below in conjunction with the attached FIG. 1, which is a schematic flowsheet of a comprehensive embodiment of the invention.

Figure 1:
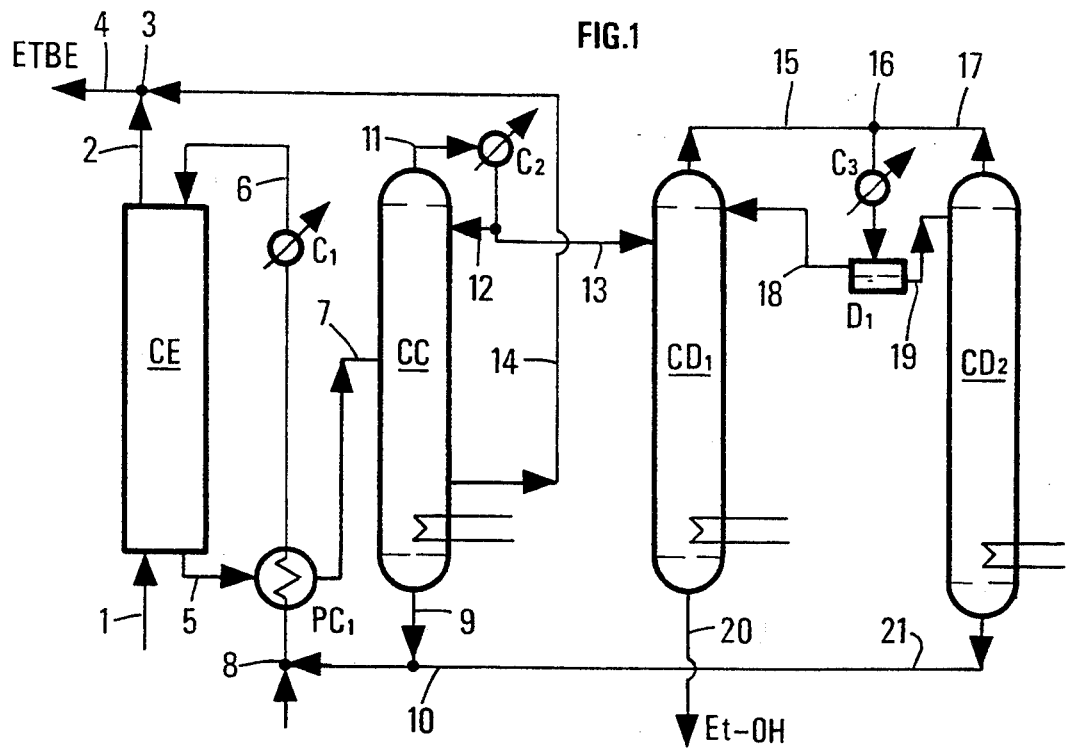

The charge comprising the mixture of ETBE and ethanol to be separated is sent by line 1 into an extraction column CE at a pressure $p_1$ of ca. 1 to 2 bar, generally at a temperature of 50 to 70 degrees C., for example ca. 60 degrees C., at the base of the said column. The water which constitutes the extraction solvent is supplied by line 6 at the column head under the same conditions of temperature and pressure. An extraction ratio of 2 to 5 moles of water per mole of charge is generally used.

The "raffinate" phase comprising ETBE saturated in water leaves overhead through line 2 and is mixed at 3 with the ETBE phase, also saturated with water, which has settled on the trays of column CC which concentrates the ethanol/water mixture, whence it is drawn off by line 14. The mixture of the two streams is collected by line 4.

The thus-separated ETBE is generally at least 98.8% pure by weight. It contains traces of water. If one wishes to obtain pure ETBE, it is necessary to provide for a subsequent dehydration, using any suitable means, for example screen drying.

Withdrawn at the base of the extraction column CE through line 5, the "extract" phase, which contains ca. 75% weight water, ca. 22% by weight ethanol and ca, 3% by weight ETBE, is heated, preferably by passage into the pre-heating exchanger PC 1, and sent by line 7 into the concentration column CC at pressure $p_1$. The concentration column CC generally operates between a base temperature of 100 to 120 degrees C. and an overhead temperature of 78 to 85 degrees C. The distillate which leaves through line 11 comprises a mixture whose composition is close to that of the ethanol/water azeotrope at pressure $p_1$ (i.e. ca. 9.1% by weight of water and ca. 90.9% by weight of ethanol), but which still contains a very small proportion of ETBE. This distillate is condensed in condenser $C_2$, the condensate being partly sent, by way of reflux, to the head of the said concentration column through line 12 and partly sent, through line 13, to the heteroazeotropic distillation column CD1 at pressure $p_1$.

An ETBE phase, saturated in water, which has settled on the trays of the concentration column CC, is drawn off through line 14. As already described above, this ETBE phase is mixed at 3 with the ETBE phase leaving the head of the extraction column CE through line 2.

An effluent comprising essentially water and traces of ethanol is drawn off at the base of the concentration column CC through line 9; it is mixed at 10 with the residue of distillation column CD 2, supplied by line 21. The resultant stream may also receive supplementary water at 8. It is cooled for example by passage into exchanger PC 1, and in the condenser C1, before supplying extraction column CE through line 6, as already indicated above.

The ethanol/water mixture leaving the head of the concentration column CC, which still contains a very small proportion of ETBE, is then separated into ethanol and water in a heteroazeotropic distillation zone using ETBE as azeotroping agent.

The ethanol/water mixture to be separated supplies, through line 13, a first distillation column CD 1 operating generally at pressure $p_1$, between a base temperature of 78 to 85 degrees C. and an overhead temperature of 64 to 70 degrees C.

The distillate leaving overhead through line 15 has a composition close to that the ternary ethanol/water/ETBE azeotrope at pressure $p_1$, i.e. at 1 bar, ca. 13% by mole of water, 27% by mole of ethanol and 60% by mole of ETBE, and is combined at 16 with the distillate leaving overhead at the second distillation column CD 2, through line 17, with a composition of ca. 82% by mole of ethanol, 17% by mole of water and 1% by mole of ETBE. The resultant vapor is then sent into the condenser $C_3$ where it is cooled, generally to a temperature of ca. 45 to 65 degrees C., more particularly to a temperature of ca. 54 degrees C., then passed into the decanter D1 where it separates into two phases: a phase rich in ETBE, which is sent back through line 18, by way of reflux, to the head of column CD1; and a phase rich in water which supplies column CD2 through line 19.

Column CD2 generally operates at pressure $p_1$, between a base temperature of 100 to 120 degrees C. and a head temperature of 94 to 110 degrees C.

The ethanol is collected at the base of column CD1, through line 20, with a purity of ca. 99% by mole, the remainder comprising water and ETBE. The resultant loss of ETBE can be compensated for by a supplement provided for example at condenser $C_3$.

Practically pure water emerges at the base of column CD2 through line 21. It is combined at 10 with the effluent from the base of the concentration column CC, to supply water to the extraction column EC through line 6.

The unit formed by the two distillation columns CD1 and CD2 and decanter D1, laid out as described above, can, considered separately, constitute a process for separating water and ethanol from their mixtures, in particular of a composition close to the azeotrope at the pressure considered.

The process of the invention for separating ETBE, as described above, can be advantageously integrated into a complete process for producing ETBE through etherification by means of ethanol of the isobutene contained in a steam-cracking, catalytic cracking or isobutane dehydrogenation $C_a$ cut.

Figure 2:
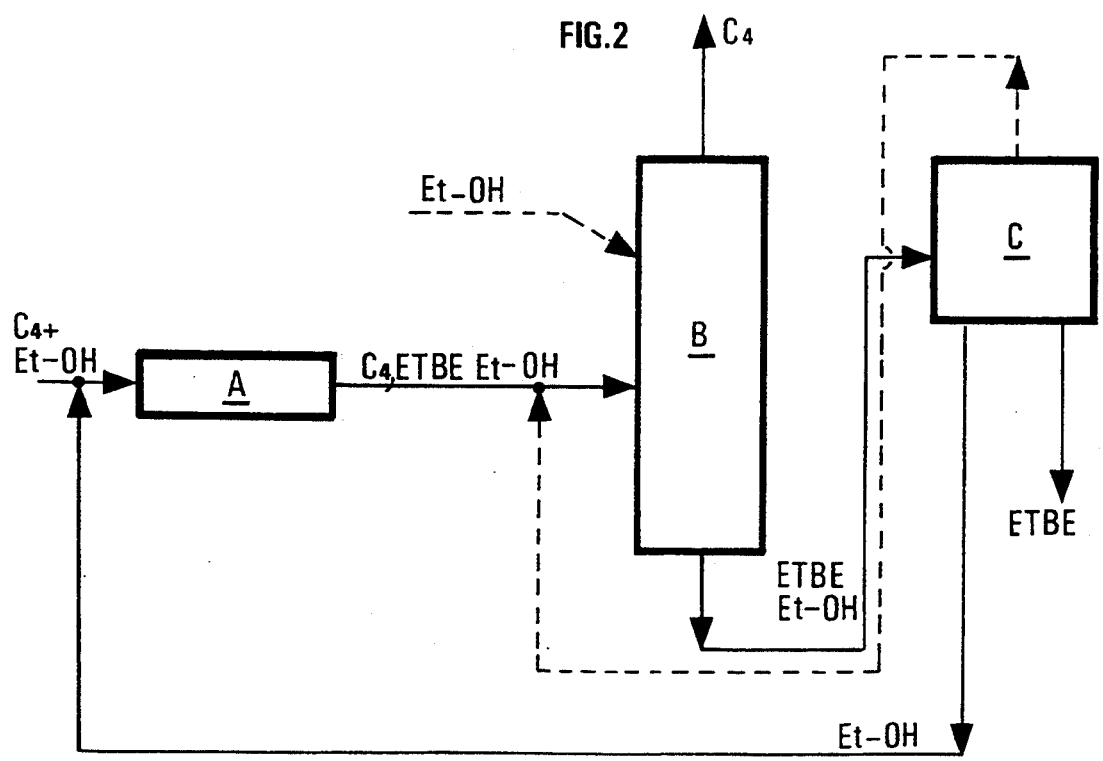
FIG. 2, on the other hand is a schematic flowsheet depicting how the invention can be integrated into an overall process for producing ETBE. The pressures indicated in the present description are absolute pressures expressed in bars (1 bar=0.1 MPa).

The process for producing ETBE, described in conjunction with the scheme of the attached FIG. 2, then comprises the following stages: in a zone A, contact is established under reaction conditions between ethanol and a steam-cracking, catalytic cracking or isobutane dehydrogenation $C_4$ cut; the product from the reaction zone A contains principally ETBE, ethanol, $C_4$ hydrocarbons other than isobutene and non-reacted isobutene. This product is sent into a distillation zone B, where the $C_4$ hydrocarbons which are very impoverished in isobutene are separated overhead and a mixture of ETBE and ethanol at the base. If one desires a more complete elimination of the isobutene one can implement, instead of a single distillation B, a reactive distillation $B^1$, using an ethanol supplement as indicated by dotted lines in FIG. 2. In all cases, the mixture of ETBE and ethanol, collected at the base of zone B, is sent into a zone C where the separation process of the invention, for example, as shown in FIG. 1, is carried out.

From zone C, the collected purified ethanol is advantageously recycled as a supplement to the reaction zone A and/or to reactive distillation zone $B^1$.

EXAMPLE

The following example illustrates the invention.

The charge to be treated contains 80% by weight of ETBE and 20% by weight of ethanol.

Used are:
a stainless-steel liquid-liquid extractor (column CE), 45 mm in diameter, having 10 perforated trays spaced 10 cm apart;
a stainless-steel first distillation column (concentration column), 100 mm in diameter, comprising 16 perforated trays 5 cm apart;
a stainless-steel distillation column CD1, 50 mm in diameter comprising 48 perforated downcomer trays 5 cm apart;
a stainless-steel distillation column CD2, 25 mm in diameter, comprising 6 perforated downcomer trays 5 cm apart; and a 15.5-liter decanter.

The apparatus is laid out as shown in the diagram of the attached FIG. 1.

The charge is introduced into the extractor at the 10th tray (the trays being counted from the top downwards) at a flow-rate of 8.21 kg/hour and a pressure of 1 bar. The water is introduced at the first tray at the temperature of 60 degrees C., a flow-rate of 5.76 kg/hour and a pressure of 1 bar.

The raffinate emerges at the head of the extractor at a flow-rate of 6.38 kg/hour and contains 98.9% by weight of ETBE and 1.1% by weight of ethanol.

The extract containing 74.9% by weight of water, 21.6% by weight of ethanol and 3.5% by weight of ETBE is sent at a flow-rate of 7.60 kg/hour into the concentration column at the 6th tray.

The temperature of the column ranges between 99.5 degrees C. at the base and 73.5 degrees C. at the head.

A product containing more than 99.99% of water and traces of ethanol is collected at the base of the column at a flow-rate of 5.53 kg/hour.

The distillate containing 9.1% by weight of water and 90.9% by weight of ethanol is condensed. A fraction of the condensate is returned to the head of the concentration column at a flow-rate of 4.68 kg/hour, by way of reflux, and the remainder at a flow-rate of 1.81 kg/hour to the head of distillation column CD1.

10 kg of ETBE are introduced at the decanter at the start.

Column CD1 is supplied at the 6th tray. The temperature of the column ranges between 78 degrees C. at the base and 64 degrees C. at the head.

A product containing 99.1% by weight of ethanol, 0.6% by weight of ETBE and 0.3% by weight of water is collected at the base of column CD1 at a flow-rate of 1.66 kg/hour.

The distillate is combined with that of distillation column CD2, and their mixture is condensed, then sent to the decanter (liquid flow-rate at the inlet 15.9 kg/hour).

From the decanter, an upper-phase reflux (flow-rate 15.5 kg/hour) is sent to column CD1 and a lower-phase reflux (flow rate 0.4 kg/hour) to column CD2, at a pressure of 1 bar.

The temperature of column CD2 ranges between 99.7 degrees C. at the base and 94.6 degrees C. at the head.

A product containing more than 99.99% by weight water and some ppm of ethanol is collected at the base of this column at a flow-rate of 0.16 kg/hour.

This product, mixed with the base product of the concentration column, can, after any water supplement, advantageously constitute the Feed-water for the extractor.

We claim:

1. A process for separating ethyl tert-butyl ether and ethanol, which comprises:
    (1) an extraction stage comprising introducing a charge, consisting essentially of a mixture of ethyl tert-butyl ether and ethanol, into an extraction zone, introducing water as an extraction solvent into the extraction zone and therefrom collecting a raffinate, consisting essentially of ethyl tert-butyl ether saturated in water, and an extract comprising an ethanol and water mixture containing ethyl tert-butyl ether;
    (2) a concentration stage comprising passing the extract from stage (1) into a concentration zone, withdrawing therefrom an overhead product having a composition close to that of an azeotropic ethanol and water composition at the head, a residue consisting essentially of water at the base, and a phase consisting essentially of ethyl tert-butyl ether at a withdrawal point between the head and the base and condensing said overhead product to obtain a distillate; and
    (3) a heteroazeotropic distillation stage having first and second distillation zones using ethyl tert-butyl ether as an azeotroping agent, comprising passing the distillate from the concentration stage into a first distillation zone and collecting therefrom a residue at the base consisting essentially of ethanol and an overhead vapor at the head, combining the overhead vapor with vapor from the head of the second distillation zone, condensing the resultant combined vapor, and passing the resultant condensate into a decanter, separating said condensate into an upper phase, rich in ethyl tert-butyl ether, and a lower phase, rich in water, passing the upper phase as reflux to the head of the first distillation zone as the azeotroping agent, passing the lower phase as reflux to the head of the second distillation zone, and collecting from the second distillation zone a residue consisting essentially of water.

2. The process of claim 1, wherein the charge contains from 5 to 50% by weight of ethanol.

3. The process of claim 1, wherein the charge contains from 10 to 30% by weight of ethanol.

4. The process of claim 1, wherein in stage (1) the extraction zone comprises an extraction column operating at a pressure of about 1 to 2 bar, at a temperature of 50 to 70 degrees C. and with an extraction ratio of 2 to 5 moles of water per mole of charge; wherein in stage (2) the concentration zone comprises a concentration column operating at a pressure of about 1 to 2 bar, between a base temperature of 100 to 120 degrees C. and a head temperature of 78 to 85 degrees C.; wherein, in stage (3), the first distillation zone comprises a first distillation column operating at a pressure of about 1 to 2 bar, between a base temperature of 78 to 85 degrees C. and a head temperature of 64 to 70 degrees C. wherein the second distillation zone comprises a second distillation column operating at a pressure of about 1 to 2 bar and between a base temperature of 100 to 120 degrees C. and a head temperature of 94 to 110 degrees C. and wherein the combined vapor from the head vapors of both distillation columns is condensed by cooling to a temperature of about 45 to 65 degrees C., before being fed into the decanter.

5. The process of claim 1, wherein the separated ethyl tert-butyl ether has a purity of at least 98.8% by weight.

6. The process of claim 1, wherein the separated ethanol has a purity of about 99% by weight.

7. The process of claim 1, which further comprises combining the phase consisting essentially of ethyl tert-butyl ether collected at a withdrawal point between the head and the base of the concentration zone with the raffinate of the extraction stage (1).

8. The process of claim 7, which further comprises combining the residue from the second distillation column consisting essentially of water and the residue from the concentration zone consisting essentially of water and, optionally, a supplemental amount of water, and passing the combination to the head of the extraction zone as the extraction solvent.

9. The process of claim 1, Which further comprises combining the residue from the second distillation column consisting essentially of water and the residue from the concentration zone consisting-essentially of water and, optionally, a supplemental amount of water, and passing the combination to the head of the extraction zone as the extraction solvent.

10. The process of claim 1, wherein, during start-up of the process, ethyl tert-butyl ether is fed into the heteroazeotropic distillation stage.

11. The process of claim 10, wherein, during start-up of the process, ethyl tert-butyl ether is fed into the decanter in the heteroazeotropic distillation stage.

12. The process of claim 1, wherein the extract from the extraction stage (1) comprises about 3 to 3.5% by weight of ethyl tert-butyl ether.

13. A process for producing ethyl tert-butyl ether through etherification by ethanol of the isobutene contained in a steam-cracking, catalytic cracking or isobutane dehydrogenation $C_4$ cut, comprising contacting ethanol and the isobutene-containing cut, in a reaction zone A, under reaction conditions such that the product from the reaction zone A, contains ethyl tert-butyl ether, ethanol, $C_4$ hydrocarbons including non-reacted isobutene; sending the product from reaction zone A into a distillation zone B, collecting the $C_4$ hydrocarbons including the non-reacted isobutene overhead and a mixture of ethyl tert-butyl ether and ethanol at the base; sending the mixture into a separation zone C and conducting therein a process for separating ethyl tert-butyl ether and ethanol, which comprises:

(1) an extraction stage comprising introducing a charge, consisting essentially of a mixture of ethyl tert-butyl ether and ethanol, into an extraction zone, introducing water as an extraction solvent into the extraction zone and therefrom collecting a raffinate, consisting essentially of ethyl tert-butyl ether saturated in water, and an extract comprising an ethanol and water mixture containing ethyl tert-butyl ether;

(2) a concentration stage comprising passing the extract from stage (1) into a concentration zone, withdrawing therefrom an overhead product having a composition close to that of an azeotropic ethanol and water composition at the head, a residue consisting essentially of water at the base, and a phase consisting essentially of ethyl tert-butyl ether at a withdrawal point between the head and the base and condensing said overhead product to obtain a distillate; and (3) a heteroazeotropic distillation stage having first and second distillation zones using ethyl tert-butyl ether as an azeotroping agent, comprising passing the distillate from the concentration stage into a first distillation zone and collecting therefrom a residue at the base consisting essentially of ethanol and an overhead vapor at the head, combining the overhead vapor with vapor from the head of the second distillation zone, condensing the resultant combined vapor, and passing the resultant condensate into a decanter, separating said condensate into an upper phase, rich in ethyl tert-butyl ether and a lower phase, rich in water, passing the upper phase as reflux to the head of the first distillation zone as the azeotroping agent, passing the lower phase as reflux to the head of the second distillation zone, and collecting from the second distillation zone a residue consisting essentially of water.

14. The process of claim 13, wherein the purified ethanol from separation zone C is recycled to the reaction zone A.

15. The process of claim 13, wherein the extract from the extraction stage (1) comprises about 3 to 3.5% by weight of ethyl tert-butyl ether.

16. In a process for separating a composition comprising ethanol and water having a composition close to that of an azeotropic ethanol and water composition in a heteroazeotropic distillation stage, the improvement wherein ethyl tert-butyl ether is used as an azeotroping agent, which improved process comprises:

introducing said ethanol and water composition and ethyl tert-butyl ether into a first distillation zone, collecting therefrom a residue at the base consisting essentially of ethanol and a vapor from the head, combining the vapor with the vapor from the head of a second distillation zone, condensing the resultant combined vapor, passing the resultant condensate into a decanter, separating the condensate in the decanter into an upper phase rich in ethyl tert-butyl ether and a lower phase rich in water, passing the upper phase in reflux to the head of the first distillation zone as the azeotroping agent, passing the lower phase as reflux to the head of the second distillation zone, and collecting from the second distillation zone a residue consisting essentially of water.

17. The process of claim 16, wherein the first distillation zone comprises a first distillation column operating at a pressure of about 1 to 2 bar and between a base temperature of 78 to 85 degrees C. and a head temperature of 64 to 70 degrees C.; wherein the second distillation zone, comprises a second distillation column operating at a pressure of about 1 to 2 bar and between a base temperature of 100 to 120 degrees C. and a head temperature of 94 to 110 degrees C.; and, wherein the combined vapor from the head vapors of both distillation columns is condensed by cooling to a temperature of about 45 to 65 degrees C. before being fed into the decanter.

18. The process of claim 16, wherein ethanol is collected as a residue from the first distillation zone with a purity of about 99% by mole and water is collected as a residue from the second distillation zone with a purity of 99.9% by weight.

19. A process for producing ethyl tert-butyl ether through etherification by ethanol of the isobutene contained in a steam-cracking, catalytic cracking or isobutane dehydrogenation $C_4$ cut, comprising contacting ethanol and the isobutene-containing cut, in a reaction zone A, under reaction conditions such that the product from the reaction zone A, contains ethyl tert-butyl ether, ethanol and $C_4$ hydrocarbons including non-reacted isobutene; sending the product from reaction zone A into a reactive distillation zone $B^1$, introducing ethanol into the reactive distillation zone under reaction conditions such that the ethanol reacts with the non-reacted isobutene, collecting the $C_4$ hydrocarbons including the non-reacted isobutene overhead and a mixture of ethyl tert-butyl ether and ethanol at the base; sending the mixture into a separating zone C and conducting therein a process for separating ethyl tert-butyl ether and ethanol, which comprises:

(1) an extraction stage comprising introducing a charge, consisting essentially of a mixture of ethyl tert-butyl ether and ethanol, into an extraction zone, introducing water as an extraction solvent into the extraction zone and therefrom collecting a raffinate, consisting essentially of ethyl tert-butyl ether saturated in water, and an extract comprising an ethanol and water mixture containing of ethyl tert-butyl ether;

(2) a concentration stage comprising passing the extract from stage (1) into a concentration zone, withdrawing therefrom an overhead product having a composition close to that of an azeotropic ethanol and water composition at the head, a residue consisting essentially of water at the base, and a phase consisting essentially of ethyl tert-butyl ether at a withdrawal point between the head and the base and condensing said overhead product to obtain a distillate; and (3) a heteroazeotropic distillation stage having first and second distillation zones using ethyl tert-butyl ether as azeotroping agent, comprising passing the distillate from the concentration stage into a first distillation zone and collecting therefrom a residue at the base consisting essentially of ethanol and overhead vapor combining the overhead vapor at the head, with the vapor from the head of a second distillation zone, condensing the resultant combined vapor, and passing the resultant condensate into a decanter, separating the condensate into an upper phase, rich in ethyl ether and a lower phase, rich in water, passing the upper phase in reflux to the head of the first distillation zone as the azeotroping agent, passing the lower phase as reflux to the head of the second distillation zone, and collecting from the second distillation zone a residue consisting essentially of water.

20. The process of claim 19, wherein the purified ethanol from separation zone C is recycled to reactive distillation zone $B^1$.

21. The process of claim 19, wherein the extract from the extraction stage (1) comprises about 3 to 3.5% by weight of ethyl tert-butyl ether.

* * * * *